United States Patent [19]

Durette et al.

[11] Patent Number: 4,663,344

[45] Date of Patent: May 5, 1987

[54] ANTI-INFLAMMATORY AND ANALGESIC 3-HYDROXYBENZO[b]THIOPHENE DERIVATIVES, COMPOSITIONS, AND METHOD OF USE THEREFOR

[75] Inventors: Philippe L. Durette, New Providence; Bruce E. Witzel, Westfield; Kathleen M. Rupprecht, Cranford; Allan N. Tischler, Westfield, all of N.J.; Timothy F. Gallagher, Harleysville, Pa.

[73] Assignee: Merck & Co., Inc., Rahway, N.J.

[21] Appl. No.: 710,727

[22] Filed: Mar. 11, 1985

[51] Int. Cl.[4] .................. A61K 31/38; A61K 31/415; C07D 333/64; C07D 409/04

[52] U.S. Cl. .................... 514/443; 514/337; 514/397; 514/422; 546/274; 548/336; 548/525; 549/52; 549/54; 549/55; 549/56

[58] Field of Search ............... 546/274; 548/336, 525; 549/52, 54, 55, 56; 514/337, 397, 422, 443

[56] References Cited

U.S. PATENT DOCUMENTS 3,954,748  5/1976  Thominet .............................. 549/52
4,410,539 10/1983  Cross et al. ........................ 548/336

Primary Examiner—John M. Ford
Assistant Examiner—J. G. Mullins
Attorney, Agent, or Firm—Theresa Y. Cheng; Michael C. Sudol

[57] ABSTRACT

3-Hydroxybenzo[b]thiophene derivatives, such as 2-aralkyl, 2-alkyl and 2-alkenyl-3-hydroxybenzo[b]-thiophenes, were prepared by, among other methods, ring closure of 2-(2-carboxy-phenylthio)-α-substituted acetic acids. These compounds are found to be useful in the treatment of pain, fever, inflammation, arthritic conditions, asthma, allergic disorders, skin diseases, cardiovascular disorders, psoriasis, inflammatory diseases and other prostaglandin and/or leukotriene mediated diseases.

21 Claims, No Drawings

ANTI-INFLAMMATORY AND ANALGESIC 3-HYDROXYBENZO[b]THIOPHENE DERIVATIVES, COMPOSITIONS, AND METHOD OF USE THEREFOR

BACKGROUND OF THE INVENTION

This invention relates to benzothiophenes, particularly 3-hydroxybenzothiophenes, having the 2-carbon side chains, for example, 3-acetoxy-2-butyl-5-chlorobenzo[b]thiophene and its 2-benzyl analog.

These novel benzothiophenes are found to be either specific 5-lipoxygenase or dual cyclooxygenase/5-lipoxygenase inhibitors and are therefore useful in the treatment of prostaglandin and/or leukotriene mediated diseases.

Among various potent biological mediators derived from the oxygenation of arachidonic acid, prostaglandins and leukotrienes have been linked to various diseases. Notably, the biosynthesis of prostaglandins has been identified as a cause of inflammation, arthritic conditions and pain, and the formation of leukotrienes has been connected to immediate hypersensitivity reactions and pro-inflammatory effects. It has been established that arachidonic acid undergoes oxygenation via two major enzymatic pathways:

(1) The pathway catalyzed by the enzyme cyclooxygenase; and (2) The pathway catalyzed by the enzyme 5-lipoxygenase.

Interruption of these pathways by enzyme inhibition has been explored for effective therapy. For example, non-steroidal anti-inflammatory drugs (NSAID's) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson *Science*, 220, 568 (1983); D. Bailey et al, *Ann. Rpts. Med. Chem.*, 17, 203 (1982)).

DETAILED DESCRIPTION OF THE INVENTION

A. Scope of the Invention

The present invention relates to novel compounds of formula (I):

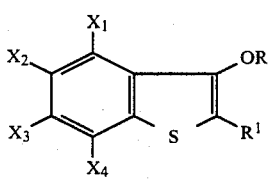

or a pharmaceutically acceptable salt thereof wherein $X_1$, $X_2$, $X_3$, and $X_4$ independently are:

(1) Q, where Q is H; loweralkyl, especially $C_{1-6}$ alkyl; haloloweralkyl, especially fluoro or chloro $C_{1-6}$ alkyl such as trifluoromethyl; phenyl of formula

or naphthyl; or imidazole of formula

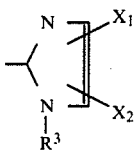

(2) halo, especially chloro, fluoro, or bromo;

(3) loweralkenyl, especially $C_{2-6}$ alkenyl, such as ethenyl and allyl;

(4) loweralkynyl, especially $C_{2-6}$ alkynyl, for example, ethynyl or n-butynyl;

(5)

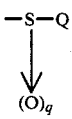

wherein q is an integer of 0 to 2;

(6) —OQ;

(7) —CHQCOQ$^1$, where Q$^1$ is Q and can be the same as or different from Q;

(8) —CHQCOOQ$^1$;

(10) —CH$_2$SQ or —CHQSQ$^1$;

(11) —CH$_2$OQ or —CHQOQ$^1$;

(12) —COQ;

(13) —COOQ;

(14) —OCOQ;

(15) —NQQ$^1$;

(16) —NQCOQ$^1$;

(17) —NQ(OQ$^1$);

(18) —NQ(SQ$^1$);

(19) —NQSO$_2$Q$^1$;

(20) —SO$_2$NQQ$^1$;

(21) —CN;

(22) —NO$_2$;

(23) —CONQQ$^1$;

(24) —NO;

(25) —CSQ;

(26) —CSNQQ$^1$;

(27) —CF$_2$SQ;

(28) —CF$_2$OQ; or

(29) —NQCONHQ$^1$ or —NQCONQ$^1$Q$^2$;

$R^1$ is (a) H;

(b) loweralkyl, especially $C_{1-6}$ alkyl, such as methyl, ethyl, i-propyl, n-propyl, t-butyl, n-butyl, i-pentyl, n-pentyl, and n-hexyl;

(c) aryl, especially $C_{6-14}$ aryl, e.g., naphthyl, anthryl, phenyl or substituted phenyl of formula

(d) lowercycloalkyl, especially $C_{3-6}$ cycloalkyl, e.g., cyclopropyl, cyclopentyl, and cyclohexyl;

(e) haloloweralkyl, especially halo $C_{1-6}$ alkyl, e.g. $-CF_3$, $-CHF_2$, $-CF_2CF_3$;

(f) heteroaryl or heteroaryl substituted with $X_1$ and $X_2$ especially pyridyl, imidazole, pyrryl, furyl or thienyl wherein $X_1$ and $X_2$ are as previously defined;

(g) benzyl of formula

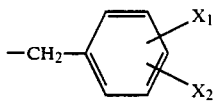

(h) loweralkynyl, especially $C_{1-6}$ alkynyl, such as $HC\equiv C-$; $CH_3-C\equiv C-$, or $HC\equiv C-CH_2-$;

(i) loweralkenyl, especially $C_{1-6}$ alkenyl, such as $CH_2=CH-$, $CH_3CH=CH-$, $CH_2=CHCH_2-$, $CH_3CH=CH-CH_2-$, $(CH_3)_2C=CH-$ or $-CH=CHCOOR$ wherein $R^2$ is loweralkyl, especially $C_{1-6}$alkyl, (j) aralkenyl of formula

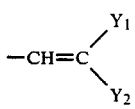

wherein $Y_1$ and $Y_2$ independently are phenyl and heteroaryl as previously defined;

(k) aralkynyl of formula $-C\equiv C-Y_1$ (l)

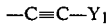

wherein m is an integer of 1-6 and $R^3$ is H, $C_{1-6}$alkyl, $C_{6-14}$aryl, $C_{3-6}$cycloalkyl or halo$C_{1-6}$alkyl;

(m) $-(CH_2)_mOR^3$;

(n)

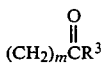

(o) $-(CH_2)_mNR^3R^4$ wherein $R^4$ can be the same or different from $R^3$ and $R^4$ is $R^3$;

(p)

(q) $-(CH_2)_mCOOR^3$; or (r)

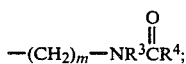

R is (a) H;
(b) $-COR^3$;
(c) $-COOR^3$;
(d) $-CONR^3R^4$;
(e) $-COSR^3$;
(f) $-(CH_2)_mCOR^3$;
(g) $-(CH_2)_mOR^3$;
(h) $-(CH_2)_mOCOOR^3$;
(i) $-(CH_2)_mNR^3R^4$;
(j) $-(CH_2)_mNR^3COR^4$;
(k) loweralkyl as previously defined;
(l) lowercycloalkyl as previously defined; or
(m) haloloweralkyl as previously defined.

Preferably, an enzyme inhibitor of this invention is of formula:

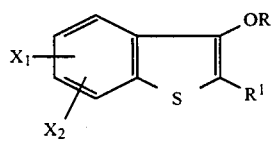

wherein $X_1$, $X_2$, R and $R^1$ are as previously defined.

More preferably, an enzyme inhibitor of this invention is of formula:

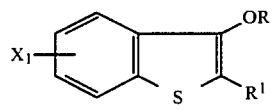

wherein
$X_1$ and $X_2$ independently are
(a) H;
(b) $C_{1-6}$alkyl;
(c) halo;
(d) halo-$C_{1-6}$-alkyl, e.g. $CF_3$;
(e) phenylalkenyl of formula

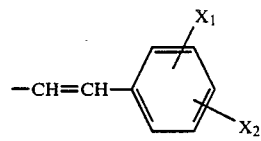

(f) OH;
(g)

$-O\overset{O}{\underset{\|}{C}}CH_3$;

(h) $-OC_{1-6}$alkyl; or
(i) $-OC_{1-6}$alkylphenyl;

$R^1$ is
(a) $C_{1-6}$alkyl;
(b) phenyl of formula

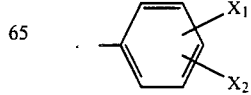

wherein $X_1$ and $X_2$ independently are halo, trifluoromethyl, methoxy, methyl, $CH_3CO-$, methylthio, or acetoxy;

(c) benzyl of formula

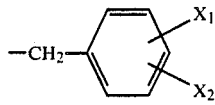

wherein $X_1$ and $X_2$ are as defined above in (b);

(d)

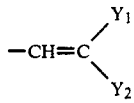

as previously defined; or (e) $C_{1-6}$alkenyl as previously defined;

R is (a) H;
(b) $-COCH_3$;
(c) $C_{1-6}$alkyl; or
(d) benzyl as previously defined.

B. Preparation of the Compounds of the Invention

The compounds of the present invention are prepared from known starting materials via various procedures, for example, methods as described in the following schemes:

Method A: Cyclization of
α-(o-carboxyphenylthio)-alkanoic or -aralkanoic acid

An appropriately substituted α-(o-carboxyphenylthio)-alkanoic or aralkanoic acid (II) is treated with a metal salt of an organic acid such as anhydrous sodium acetate, and an organic acid anhydride, such as acetic anhydride, at elevated temperatures (60° C. to 130° C.) for from 10 minutes to several hours to provide the 2-substituted-3-acetoxybenzo[b]thiophene derivative (III), according to the following scheme:

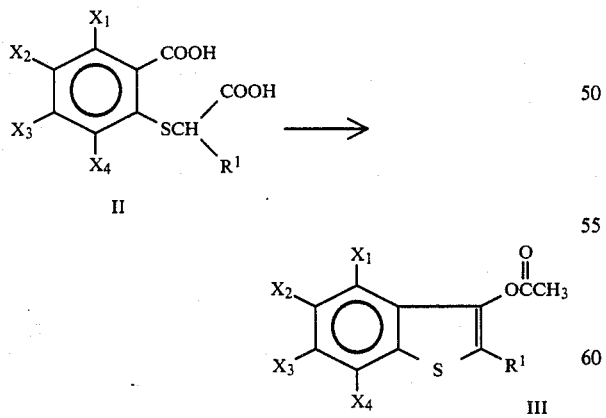

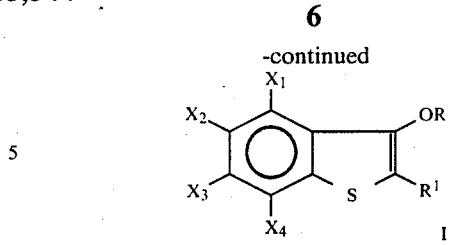

Acidic or basic hydrolysis of the benzo[b]thiophenol acetate (III), followed by appropriate derivatization of the 3-hydroxy group via conventional methods of alkylation or acylation affords the desired 2-substituted 3-hydroxybenzo[b]thiophene derivative (I).

The optionally substituted α-(o-carboxyphenylthio)alkanoic or aralkanoic acids are obtained by condensation of an optionally substituted o-carboxythiophenol with an α-halo-(preferably, chloro- or bromo)alkanoic or aralkanoic acid in the presence of base followed by acidification. The requisite thiophenols are either known or can be made by known methodologies, such as, conversion of a phenol into a thiophenol via thermal rearrangement of the phenol O-dimethylthiocarbamate (IV) into the S-dimethylthiocarbamate derivative (V) followed by methanolysis in the presence of sodium methoxide or basic hydrolysis to the free thiophenol, (VI) according to the following scheme:

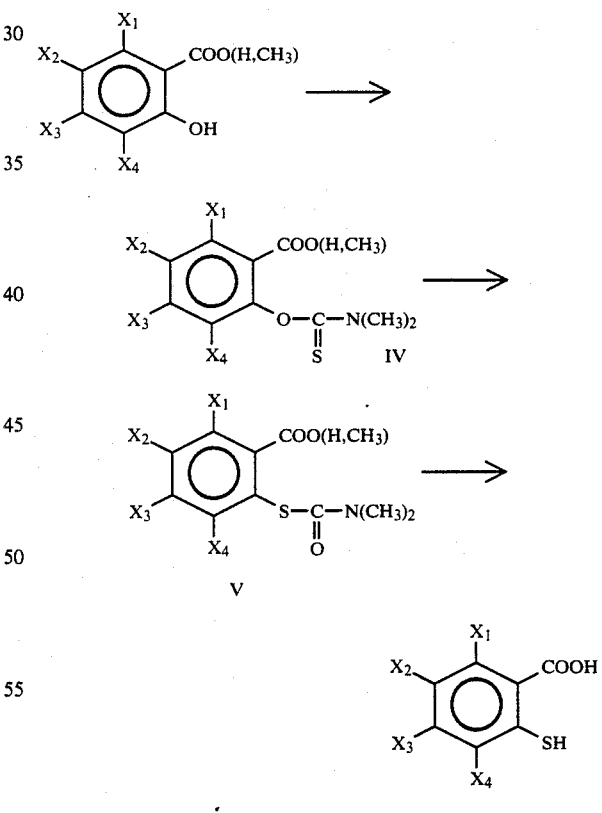

Method B: Intramolecular Condensation of an Appropriately Substituted Alkyl 2-Benzylthiobenzoate An appropriately substituted alkyl 2-benzylthiobenzoate (VII) is treated with a sufficiently strong base, such as a metal hydride, in particular, sodium hydride, in a solvent, such as N,N-dimethylformamide, dimethyl sulfoxide, or the like, at elevated temperatures (60° C. to 150° C.) for from 30 minutes to several hours, to afford directly, after acidification, the desired appropriately substituted 2-phenyl-3-hydroxybenzo[b]thiophene VIII, as shown below:

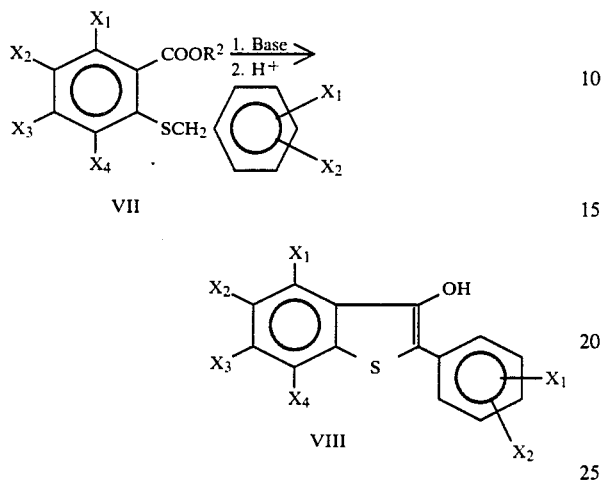

wherein $R^2$ is $C_{1-6}$ alkyl.

The requisite alkyl 2-benzylthiobenzoates are prepared by either (a) condensation of an alkyl 2-mercaptobenzoate (IX) with an appropriately substituted α-halotoluene (preferably chloro or bromo) as shown below, in the presence of a base, such as sodium methoxide.

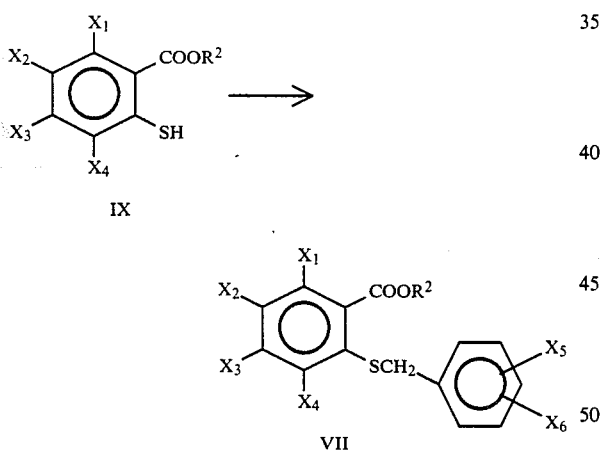

The condensation is carried out in the presence of a base, for example, sodium, methoxide in methanol, triethylamine, or pyridine in a solvent, such as chloroform, dichloromethane, tetrahydrofuran, p-dioxane, acetonitrile, or the like; or (b) nucleophilic displacement of halide in a 2-halobenzonitrile (X) with an alkali salt, preferably sodium or potassium, or an arylmethylmercaptan in a solvent, such as tetrahydrofuran, N,N-dimethylformamide, dimethylsulfoxide, or the like, followed by hydrolysis of the nitrile (XI) to the corresponding benzoic acid (XII) and esterification, e.g., methyl esterification with methanol in the presence of an acid catalyst; diazomethane; iodomethane or dimethylsulfate in the presence of a base; or with 1-aza-2-methoxy-1-cycloheptene.

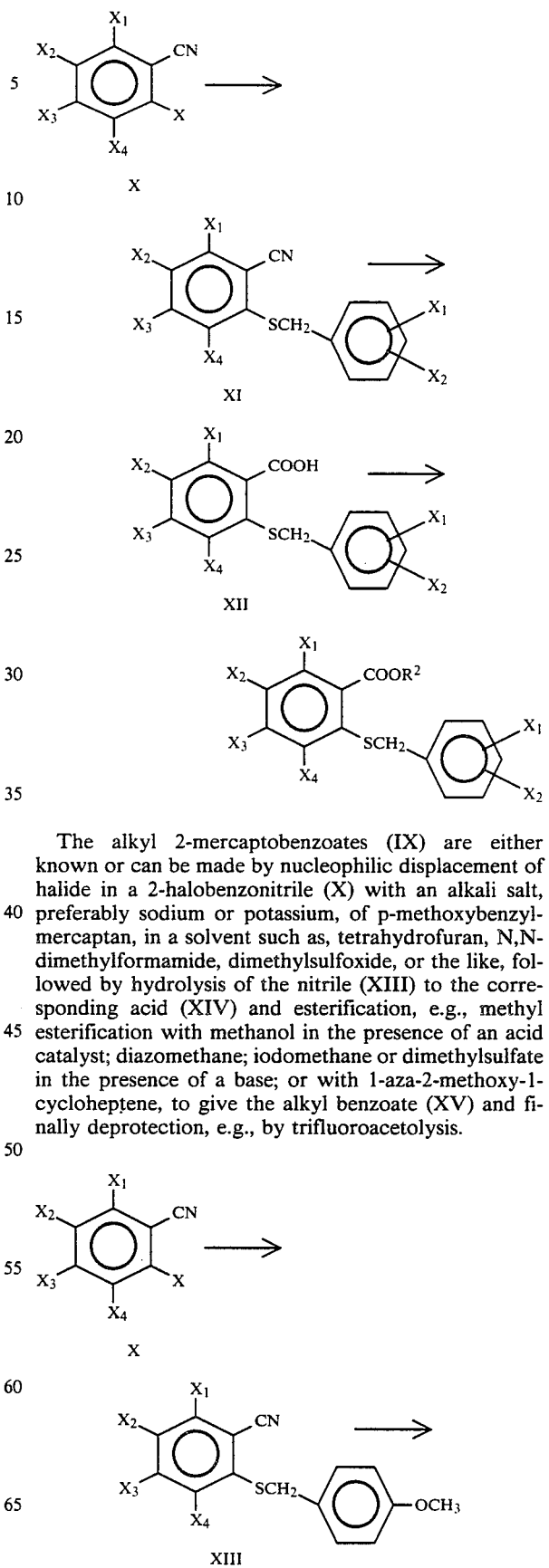

The alkyl 2-mercaptobenzoates (IX) are either known or can be made by nucleophilic displacement of halide in a 2-halobenzonitrile (X) with an alkali salt, preferably sodium or potassium, of p-methoxybenzylmercaptan, in a solvent such as, tetrahydrofuran, N,N-dimethylformamide, dimethylsulfoxide, or the like, followed by hydrolysis of the nitrile (XIII) to the corresponding acid (XIV) and esterification, e.g., methyl esterification with methanol in the presence of an acid catalyst; diazomethane; iodomethane or dimethylsulfate in the presence of a base; or with 1-aza-2-methoxy-1-cycloheptene, to give the alkyl benzoate (XV) and finally deprotection, e.g., by trifluoroacetolysis.

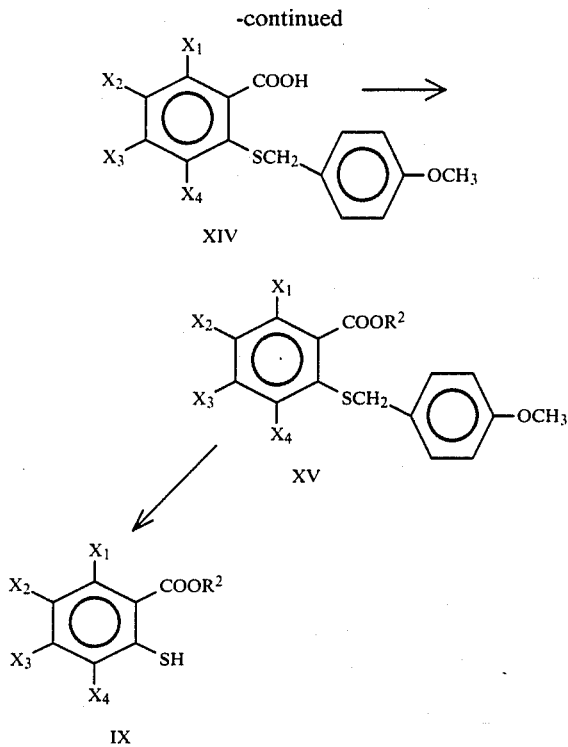

Method C: Intermolecular condensation between an appropriately substituted 2-thiobenzoate An appropriately substituted 2-thiobenzoate (XVI) is condensed with a 1-alkoxycarbonylallylhalide in the presence of a strong base similar to those described in Methods A and B. The resultant 2-(2-alkoxycarbonylvinyl)-3-hydroxybenzo[b]thiophene (XVII) is then converted to 2-(2-alkoxycarbonylvinyl)-3-alkoxybenzo[b]thiphene (XVIII) by conventional methods of alkylation and reduction.

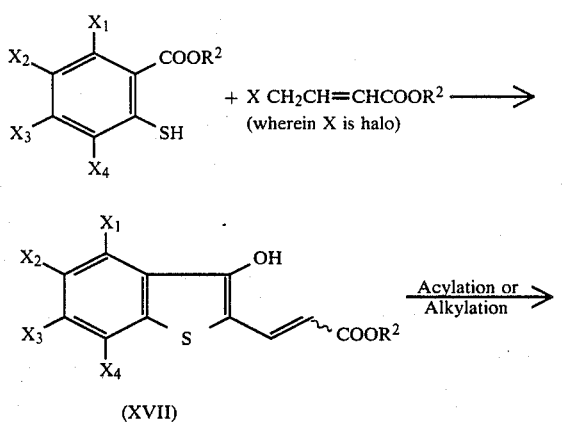

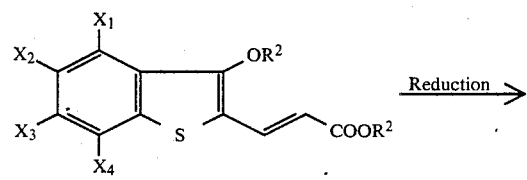

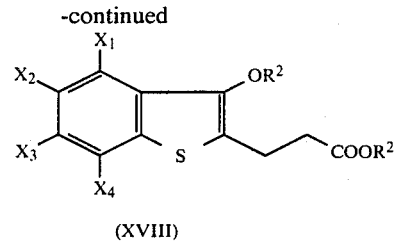

The following examples illustrate but do not limit the present invention:

EXAMPLE 1

3-Acetoxy-2-Butyl-5-Chlorobenzo[b]thiophene

Step A: Preparation of 2-(2'-carboxy-4'-chlorophenylthio)-hexanoic acid

A mixture of 5-chlorothiosalicylic acid [prepared by the process set forth in L. Katz et al., *J. Org. Chem.*, 18 (1953) 1380] (2.0 g, 9.8 mmol) and 1N aqueous sodium hydroxide (100 ml) was heated at reflux temperature for 1 hour under a nitrogen atmosphere. 2-Bromohexanoic acid (1.9 g, 9.8 mmol) was then added, and refluxing was continued for an additional hour. The mixture was cooled in an ice bath and acidified with concentrated hydrochloric acid. The acidic mixture was extracted with diethyl ether, and the combined organic layers were washed with water, saturated aqueous sodium chloride solution, dried (sodium sulfate), and evaporated. The product was obtained as a light yellow solid (2.4 g) that was used without further purification in the subsequent step below.

Step B: Preparation of 3-acetoxy-2-butyl-5-chlorobenzo[b]thiophene

A mixture of 2-(2'-carboxy-4'-chlorophenylthio)hexanoic acid (2.3 g, 7.6 mmol), anhydrous sodium acetate (1.0 g), and acetic anhydride (5 ml) was heated at 80° C. for 30 minutes. After gas evolution had ceased, the temperature was gradually raised to 120° C. which was maintained for 30 minutes. The cooled reaction mixture was then poured into water and extracted with diethyl ether. The combined ethereal extracts were washed with 1% aqueous sodium hydroxide solution, water, and saturated aqueous sodium chloride solution, dried (sodium sulfate) and evaporated. The residue was vacuum filtered through a pad of silica gel (Merck No. 7734) eluting with 25:1 hexane-ether to give 3-acetoxy-2-butyl-5-chlorobenzo[b]thiophene as a colorless oil; yield 1.1 g (40% overall from the 2-step sequence), m/z 282 (M+.).

EXAMPLE 2

3-Acetoxy-2-Benzyl-5-Chlorobenzo[b]thiophene

Employing the procedure described in Example 1, but substituting for the 2-bromohexanoic acid used in Step A thereof, an equivalent amount of 2-bromo-3-phenylpropionic acid, there were prepared in sequence:
Step A: 2-(2'-Carboxy-4'-chlorophenylthio)-3-phenylpropionic acid
Step B: 3-Acetoxy-2-benzyl-5-chlorobenzo[b]thiophene, obtained as a white crystalline solid, 32% overall yield from the 2-step sequence; m/z 316 (M+.)

EXAMPLE 3

2-Benzyl-5-Chloro-3-Hydroxybenzo[b]thiophene

A mixture of 3-acetoxy-2-benzyl-5-chlorobenzo[b]-thiophene (100 mg) and 2N aqueous sodium hydroxide (2 ml) in ethanol (1 ml) was heated at reflux temperature for 1 hour. The reaction mixture was cooled in an ice bath and acidifed with concentrated hydrochloric acid. The solid that separated out was collected by filtration, washed with water, and dried in vacuo over calcium sulfate to afford 2-benzyl-5-chloro-3-hydroxybenzo[b]-thiophene as a white solid (40 mg); m/z 274 (M+.).

EXAMPLE 4

3-Hydroxy-2-Phehyl-5-Trifluoromethylbenzo[b]thiophene

Step A: Preparation of methyl 2-benzylthio-5-trifluoromethylbenzoate

A solution of 2-benzylthio-5-trifluoromethylbenzoic acid [prepared by the procedure set forth in J. G. Lombardino and E. H. Wiseman, *J. Med. Chem.*, 13 (1970) 206–210] (22 g, 70 mmol) in thionyl chloride (10 ml) was heated at reflux temperature for 1 hour. After cooling to room temperature, excess thionyl chloride was removed by evaporation under diminished pressure. The produce was treated with methanol (25 ml) for 1 hour at reflux temperature. The cooled solution was evaporated to give methyl 2-benzylthio-5-trifluoromethylbenzoate (20 g, 88%), which was used without further purification in the subsequent step below. NMR (CDCl$_3$, 60 MHz): δ 3.92 (s, CO$_2$CH$_3$); 4.19 (s, SCH$_2$Ph) p.p.m.

Step B: Preparation of 3-Hydroxy-2-phenyl-5-trifluoromethylbenzo[b]thiophene To a suspension of sodium hyride (50% dispersion in mineral oil) (0.49 g, 10.2 mmol) in N,N-dimethylformamide (30 ml) cooled to 0° C. in an ice-bath was added dropwise with stirring a solution of methyl 2-benzylthio-5-trifluoromethylbenzoate (2.5 g, 7.7 mmol) in N,N-dimethylformamide (10 ml). The reaction mixture was stirred at 75° C. for 1.5 hours under a nitrogen atmosphere, cooled and then poured into ice containing 1N hydrochloric acid. Extraction was effected with diethyl ether. The combined organic extracts were washed three times with water, once with saturated aqueous sodium chloride solution, dried (sodium sulfate) and evaporated. The residue was subjected to chromatography on a column of silica gel (Merck No. 7734) that was eluted with 10:1 hexane-ether. Fractions containing pure product were combined and evaporated to give a white solid that was recrystallized from toluene; yield 490 mg (22%), m/z 1294 (M+.).

EXAMPLE 5

3-Acetoxy-2-Phenyl-5-Trifluoromethylbenzo[b]thiophene

3-Hydroxy-2-phenyl-5-trifluorobenzo[b]thiophene (0.30 g, 1.0 mmol) was treated with acetic anhydride (1 ml) and pyridine (10 ml) for 18 hours at room temperature. The reaction mixture was poured into ice-water and the solid product was collected by filtration, washed with water, dried by suction and then in vacuo over phosphorous pentoxide to give 3-acetoxy-2-phenyl-5-trifluoromethylbenzo[b]thiophene (0.27 g, 80% yield) as a white crystalline solid; m/z 336 (M+.).

EXAMPLE 6

3-Hydroxy-4-Methoxy-2-Phenylbenzo[b]thiophene

Step A: Preparation of Methyl 2,6-dihydroxybenzoate

Concentrated sulfuric acid (40 ml) was carefully added to a solution of 2,6-dihydroxybenzoic acid (133 g, 0.86 mol) in absolute methanol (500 ml). The reaction mixture was heated at reflux temperature for 24 hours, cooled, and evaporated. The residue was added to aa saturated sodium hydrogencarbonate solution, and the resulting solid was collected by filtration, washed with water, and dried in vacuo over phosphorus peroxide; yield 49 g (34%). NMR (CDCl$_3$, 60 MHz): δ4.02 (s, CO$_2$CH$_3$) p.p.m.

Step B: Preparation of O-2-carbomethoxy-3-hydroxyphenyldimethylthiocarbamate A solution of methyl 2,6-dihydroxybenzoate (46 g, 0.27 mol) in N,N-dimethylformamide (100 ml) was added dropwise with stirring to a suspension of sodium hydride (50% dispersion in mineral) (14.4 g, 0.30 mol) in N,N-dimethylformamide (200 ml) cooled to 0° C. in an ice bath. After stirring for 1 hour at room temperature under a nitrogen atmosphere, a solution of dimethylthiocarbamoyl chloride (49.0 g, 0.40 mol) in N,N-dimethylformamide (100 ml) was added dropwise. Stirring was continued for 4 hours at room temperature followed by 1 hour at 80° C. The reaction mixture was cooled, poured into ice-water and extracted with diethyl ether. The combined extracts were washed with water (3×), saturated aqueous sodium chloride solution, dried (sodium sulfate), and evaporated. The residue was triturated with methanol followed by petroleum ether to give O-2-carbomethyoxy-3-hydroxyphenyl dimethylthiocarbamate as a white solid, yield (16.7 g (24%).

Step C: Preparation of O-2-Carbomethoxy-3-methoxyphenyl dimethylthiocarbamate A solution of O-2-carbomethoxy-3-hydroxyphenyl dimethylthiocarbamate (1.0 g, 3.9 mmol) in N,N-dimethylformamide (10 ml) was added dropwise with stirring to a suspension of sodium hydride (0.19 g, 3.9 mmol) in N,N-dimethylformamide (15 ml) cooled to 0° C. in an ice bath. The reaction mixture was stirred for 1 hour at room temperature. Iodomethane (0.26 ml, 4.3 mmol) was added, and stirring was continued for an additional 3 hours, at which time the mixture was poured into water. Extraction with diethyl ether followed by washing of the extracts with water (3×), saturated aqueous sodium chloride solution, drying (sodium sulfate), and evaporation gave a syrup that was triturated with methanol to afford O-2-carbomethoxy-3-methoxyphenyl dimethylthiocarbamate as a white crystalline solid; yield 0.80 g (76%). NMR (CDCl$_3$, 60 MHz: δ3.30 (d, NME$_2$) p.p.m.

Step D: Preparation of S-2-carbomethoxy-3-methoxyphenyl dimethylthiocarbamate O-2-Carbomethoxy-3-methoxyphenyl dimethylthiocarbamate (2.3 g) was heated at 240° C. for 70 minutes under a nitrogen atmosphere. The dark brown solid obtained upon cooling was triturated with diethyl ether to give S-2-carbomethoxy-3-methoxyphenyl dimethylthiocarbamate, which was employed without further purification in the subsequent step below. NMR (CDCl$_3$, 60 MHz): δ3.00 (s, NME$_2$) p.p.m.

Step E: Preparation of Methyl 2-benzylthio-6-methoxybenzoate

A solution of S-2-carbomethoxy-3-methoxyphenyl dimethylthiocarbamate (1.2 g, 4.5 mmol) and sodium methoxide (0.24 g, 4.5 mmol) in methanol (10 ml) was stirred at reflux temperature under a nitrogen atmosphere for 4 hours. α-Bromotoluene (0.60 ml, 4.9 mmol) was then added, and heating was maintained for an additional hour. The cooled mixture was evaporated, and the residue partitioned between diethyl ether and water. The organic layer was separated and washed with 1% aqueous sodium hydroxide solution, water, saturated aqueous sodium chloride solution, dried (sodium sulfate), and evaporated. The residue was vacuum filtered through a pad of silica gel (Merck No. 7734), eluting successively with 10:1 and 5:1 hexane-ether. Evaporation of the appropriate fractions gave methyl 2-benzylthio-6-methoxybenzoate as a colorless syrup; yield (0.70 g, 54%); NMR (CDCl$_3$, 60 MHz): δ4.06 (s, SCH$_2$Ph) p.p.m.

Step F: Preparation of 3-hydroxy-4-methoxy-2-phenylbenzo[b]thiophene

A solution of methyl 2-benzylthio-6-methoxybenzoate (0.50 g, 1.7 mmol) in N,N-dimethylformamide (2 ml) was added dropwise with stirring under a nitrogen atmosphere to a suspension of sodium hydride (50% dispersion in mineral oil) (90 mg, 1.9 mmol) in N,N-dimethylformamide (5 ml) at room temperature. The mixture was stirred at 80° C. for 2 hours and then at 100° C. for 10 hours. The cooled mixture was then poured into ice containing 2N hydrochloric acid and extracted with diethyl ether. The combined organic layers were washed with water (3×), saturated aqueous sodium chloride solution, dried (sodium sulfate), and evaporated. The residue was vacuum filtered through a pad of silica gel (Merck No. 7734), eluting with 2:1 hexane-ether. Fractions containing pure product were evaporated, and the resulting syrup triturated with methanol to afford 3-hydroxy-4-methoxy-2-phenylbenzo[b]thiophene as a white solid; yield 0.12 g (27%); m/z 256 (M$^{30}$.).

EXAMPLE 7

3,4-Diacetoxy-2-Phenylbenzo[b]thiophene

Step A: Preparation of O-3-Acetoxy-2-carbomethoxyphenyl dimethylthiocarbamate o-2-Carbomethoxy-3-hydroxyphenyldimethylthiocarbamate (5.1 g, 20 mmol) was treated with acetic anhydride (35 ml) and pyridine (50 ml) for 18 hours at room temperature. The mixture was then poured into water and extracted with diethyl ether. The combined organic extracts were washed with 2N hydrochloric acid, saturated aqueous sodium hydrogen carbonate solution, saturated aqueous sodium chloride solution, dried (sodium sulfate9 and evaporated to give 3-acetoxy-2-carbomethoxyphenyl dimethylthiocarbamate as a white solid; yield 5.0 g (84%). NMR (CDCl$_3$, 60 MHz): δ2.24 (s, OAc); 3.32 (d, NME$_2$); 3.74 (s, CO$_2$CH$_3$) p.p.m.

Step B: Preparation of S-3-acetoxy-2-carbomethoxyphenyl dimethylthiocarbamate

O-3-Acetoxy-2-carbomethoxyphenyl dimethylthiocarbamate (5.0 g, 17 mmol) was heated at 240° C. for 20 minutes under a nitrogen atmosphere. The crude product was subjected to chromatography on a column of silica gel (Merck No. 7734), eluting successively with 2:1, 3:1, 4:1, and 5:1 etherhexane, to give S-3-acetoxy-2-carbomethyoxyphenyl dimethylthiocarbamate as a white solid; yield 1.4 g (32%). NMR (CDCl$_3$, 60 MHz): δ2.21 (s, OAc); 2.98 (s, NMe$_2$); 3.81 (s, CO$_2$CH$_3$) p.p.m.

Step C: Preparation of 2-Hydroxy-6-mercaptobenzoic acid

A mixture of S-3-acetoxy-2-carbomethoxyphenyl dimethylthiocarbamate (0.70 g, 2.7 mmol) and 20% aqueous sodium hydroxide (60 ml) in ethanol (20 ml) was stirred at reflux temperature for 18 hours. The cooled mixture was acidified by the addition of concentrated hydrochloric acid. The resulting mixture was extracted with diethyl ether, and the combined organic extracts were washed with water, saturated aqueous sodium chloride solution, dried (sodium sulfate), and evaporated to give 2-hydroxy-6-mercaptobenzoic acid as a light brown solid; yield 0.29 g (63%).

Step D: Preparation of 2-Phenyl-2-(2'-carboxy-3'-hydroxyphenylthio)-acetic acid

α-Bromophenylacetic acid (0.26 g, 1.2 mmol) was added to a solution of 2-hydroxy-6-mercaptobenzoic acid (0.20 g, 1.2 mmol) in 1N aqueous sodium hydroxide (25 ml). The reaction mixture was stirred at reflux temperature for 1 hour under a nitrogen atmosphere. The cooled reaction mixture was acidified with 2N hydrochloric acid. The solid that precipitated out was collected by filtration, washed with water, and dried in vacuo over calcium sulfate; yield 0.20 g (38%). NMR (CDCl$_3$, 60 MHz): δ4.86 (s, SCHCO$_2$H) p.p.m.

Step E: Preparation of 3,4-Diacetoxy-2-phenylbenzo[b]thiophene

A mixture of 2-phenyl-2-(2'-carboxy-3'-hydroxyphenylthio)-acetic acid (0.19 g, 0.62 mmol), sodium acetate (0.38 g) and acetic anhydride (2 ml) was heated at 60° C. for 10 minutes, with vigorous gas evolution taking place. The mixture was poured into ice-water and extracted with diethyl ether. The combined organic extracts were washed with 1% aqueous sodium hydroxide, water, dried (sodium sulfate), and evaporated. The residue was subjected to chromatography and evaporated. The residue was subjected to chromatography on a column of silica gel (Merck No. 7734), eluting with 1:1 hexane-ether to afford 3,4-diacetoxy-2-phenylbenzo[b]thiophene as a white solid; yield 29 mg (14%); m/z 326 (M$^+$.).

EXAMPLE 8

3,4-Dihydroxy-2-Phenylbenzo[b thiophene

A solution of 3,4-diacetoxy-2-phenylbenzo[b]thiophene (28 mg) in methanol (5 ml) was treated with a catalytic amount of sodium methoxide for 18 hours at room temperature. One drop of acetic acid was added, and the solution was evaporated. The residue was dissolved in dichloromeethane, filtered and the filtrate evaporated to give 3,4-dihydroxy-2-phenylbenzo[b]thiophene as a light yellow solid; yield 20 mg; m/z 242 (M+.).

EXAMPLE 9

3-Hydroxy-4-Isopropoxy-2-Phenylbenzo[b]thiophene

Employing the procedure described in Example 6, but substituting for the iodomethane used in Step C thereof, an equivalent amount of isopropyl bromide, there were prepared in sequence:

Step A: O-2-Carbomethoxy-3-isopropoxyphenyl dimethylthiocarbamate. NMR (CDCl$_3$, 60 MHz): δ3.32 (d, NME$_2$); 3.72 (d, (CH$_3$)$_2$CHCH$_2$O—); 3.80 (s, CO$_2$CH$_3$) p.p.m.

Step B: S-2-Carbomethoxy-3-isopropoxyphenyl dimethylthiocarbamate. NMR (CDCl$_3$, 60 MHz): δ3.00 (s, NMe$_2$); 3.71 (d, (CH$_3$)$_2$CHCH$_2$O); 3.86 (s, CO$_2$CH$_3$) p.p.m.

Step C: Methyl 2-benzylthio-6-isopropoxybenzoate

Step D: 3-Hydroxy-4-isopropoxy-2-phenylbenzo[b]thiophene, m/z 298 (M+.).

EXAMPLE 10

4-Benzyloxy-3-Hydroxy-2-Phenylbenzo[b]thiophene

Employing partly the procedure described in Example 6, but substituting for the iodomethane used in Step C thereof, an 'equivalent amount of α-bromotoluene, there were prepared in sequence:

Step A: O-3-Benzyloxy-2-carbomethoxyphenyl dimethylthiocarbamate; NMR (60 MHz, CDCl$_3$): δ3.33 d (NME$_2$); 3.79 s (CO$_2$CH$_3$); 5.05 s (OCH$_2$Ph) p.p.m.

Step B: S-3-Benzyloxy-2-carbomethoxyphenyl dimethylthiocarbamate; NMR (60 MHz, CDCl$_3$): δ3.02 s (NME$_2$); 3.85 s (CO$_2$CH$_3$); 5.10 s (OCH$_2$Ph) p.p.m.

Subsequently, employing the procedure described in Steps C-E of Example 7, there were prepared in sequence:

Step C: 2-Benzyloxy-6-mercaptobenzoic acid

Step D: 2-Phenyl-2-(3'-benzyloxy-2'-carboxyphenylthio)acetic acid

Step E: 3-Acetoxy-4-benzyloxy-2-phenyl benzo[b]thiophene

Finally, employing the procedure described in Example 8, there was prepared:

Step F: 4-Benzyloxy-3-hydroxy-2-phenylbenzo[b]thiophene; m/z 332 (M+.).

EXAMPLE 11

3-Hydroxy-5-Trifluoromethyl-2-(m-trifluoromethylphenyl)-Benzo[b]thiophene

Step A: Preparation of 2-(p-methoxybenzylthio)-5-trifluoromethylbenzoic acid

A solution of p-methoxybenzylmercaptan (20.0 g, 0.13 mol) and sodium methoxide (7.0 g) in N,N-dimethylformamide (55 ml) was added dropwise with stirring under a nitrogen atmosphere to a solution of 4-chloro-3-cyanobenzotrifluoride (26.7 g, 0.13 mol) in N,N-dimethylformamide (35 ml) cooled in an ice bath. After stirring for 2 hours at room temperature, the reaction mixture was poured into ice-water and extracted several times with dichloromethane. The combined organic extracts were dried (sodium sulfate) and evaporated to afford in essentially quantitative yield, 2-(4'-methoxybenzylthio)-5-trifluoromethylbenzonitrile as an oil; 60 MHZ NMR spectrum in chloroform-d was in accord with the desired structure. A mixture of the crude product in ethanol (110 ml) and 20% aqueous sodium hydroxide (450 ml) was heated at reflux temperature with stirring for 24 hours. The cooled hydrolysis mixture was concentrated, the resulting solid filtered, and washed with ether. The mother liquors were partitioned and the ethereal layer evaporated. The filtered solid was dissolved in methanol and added to the residue from the mother liquor work-up. The solution was evaporated, the resulting oil suspended in water and the aqueous mixture acidified with 6N hydrochloric acid. The precipitated solid was filtered and dried in vacuo over phosphorous pentoxide; yield 41 g (92%).

Step B: Preparation of Methyl 2-(p-methoxybenzylthio) 5-trifluoromethylbenzoate

To a mixture of 2-(p-methoxybenzylthio)-5-trifluoromethylbenzoic acid (40 g) in methanol (840 ml) was carefully added concentrated sulfuric acid (12 ml). The mixture was heated at reflux temperature for 24 hours and cooled. The crystalline solid that separated out was filtered and washed with cold methanol. The filtrate and washings were cooled to 0° C. and a second crop was obtained. The combined crops were dried in vacuo; yield 30.3 g (73%). NMR (CDCl$_3$; 60 MHz): δ4.08 (s, SCH$_2$φ) p.p.m.

Step C: Preparation of Methyl 2-mercapto-5-trifluoromethylbenzoate

A solution of methyl 2-(p-methoxybenzylthio)-5-trifluoromethylbenzoate (1.0 g, 2.8 mmol) and anisole (335 μl) in trifluoroacetic acid (10 ml) was stirred at reflux temperature for 20 minutes under a nitrogen atmosphere. The mixture was evaporated under diminished pressure and co-evaporated several times with toluene. The mercaptan was used without further purification in the subsequent step below. NMR (CDCl$_3$, 60 MHz): δ3.88 (s, CO$_2$CH$_3$) p.p.m.

Step D: Preparation of Methyl 2-(m-trifluoromethylbenzylthio)-5-trifluoromethylbenzoate The crude mercaptan from the previous step was dissolved in methanol (25 ml) and treated with sodium methoxide (152 mg, 2.8 mmol) and α'-chloro-α,α, α-trifluoro-m-xylene (491 mg, 2.52 mmol) overnight at room temperature under a nitrogen atmosphere. The reaction mixture was evaporated, and the residue taken up in dichloromethane, washed with water (2×), dried (sodium sulfate), and evaported. The syrup (890 mg) was chromatographed on a column of silica gel (Merck 7734) that was eluted with 20:1 hexane-ether. The product was crystallized from hexane; yield 650 mg (59% overall from 2-step sequence).

Step E: Preparation of 3-Hydroxy-5-trifluoromethyl-2-(m-trifluoromethylphenyl)-benzo[b]thiophene To a mixture of sodium hydride (50% dispersion in mineral oil) (91 mg, 1.69 mmol) in N,N-dimethylformamide (2 ml) at 75° C. under a nitrogen atmosphere was added dropwise with stirring a solution of methyl 2-(m-trifluoromethylbenzylthio)-5-trofluoromethylbenzoate (373 mg, 0.95 mmol) in N,N-dimethylformamide (8 ml). After stirring 30 minutes at 75° C, the mixture was poured into water (50 ml), the mixture brought to pH 5 with 2N hydrochloric acid, the product extracted with diethyl ether, the combined extracts washed with water, dried (sodium sulfate), and evaporated. The residue was chromatographed on a column of silica gel (Merck 7734, packed as a slurry in 20:1 hexane-ether). Elution with 20:1 hexane-ether containing 1% acetic acid afforded the desired product that crystallized upon standing; yield 239 mg (76%); m/z 362 (M+.).

EXAMPLE 12

3-Hydroxy-2-(m-chlorophenyl)-5-trifluoromethyl-benzo[b]thiophene

Employing the procedure described in Example 11, but substituting for the α'-chloro-α,α,α-trifluoro-m-xylene used in Step D thereof, an equivalent amount of m-chlorobenzyl bromide, there were prepared in sequence:

Step A: Methyl 2-(m-chlorobenzylthio)-5-trifluoromethylbenzoate; NMR (60 MHz, CDCl$_3$): δ3.93 s (CO$_2$CH$_3$); 4.15 s (SCH$_2$φ) p.p.m.

Step B: 3-Hydroxy-2-(m-chlorophenyl)-5-trifluoromethylbenzo[b]thiophene; m.p. 122°–125°; m/z 328 (M+.)

EXAMPLE 13

3-Hydroxy-2-(2,6-dimethylphenyl)-5-trifluoromethyl-benzo[b]thiophene

Employing the procedure described in Example 11, but substituting for the α'-chloro-α,α,α-trifluoro-m-xylene used in Step D thereof, an equivalent amount of 2,6-dimethylbenzyl chloride, there were prepared in sequence:

Step A: Methyl 2-(2,6-dimethylbenzylthio)-5-trifluoromethylbenzoate

Step B: 3-Hydroxy-2-(2,6-dimethylphenyl)-5-trifluoromethylbenzo[b]thiophene; m/z 322 (M+.)

EXAMPLE 14

3-Hydroxy-2-(p-methylphenyl)-5-trifluoromethylbenzo[b]thiophene

Employing the procedure described in Example 11, but substituting for the α'-chloro-α,α,α-trifluoro-m-xylene used in Step D thereof, an equivalent amount of α-bromo-p-xylene, there were prepared in sequence:

Step A: Methyl 2-(p-methylbenzylthio)-5-trifluoromethylbenzoate.

Step B: 3-Hydroxy-2-(p-methylphenyl)-5-trifluoromethylbenzo[b]thiophene; m/z 308 (M+.)

EXAMPLE 15

3-Hydroxy-2-(p-methoxyphenyl)-5-trifluoromethylbenzo[b]thiophene

To a mixture of sodium hydride (50% dispersion in mineral oil) (134 mg, 2.79 mmol) in N,N-dimethylformamide (3 ml) at 75° C. under a nitrogen atmosphere was added dropwise with stirring a solution of methyl 2-(p-methoxybenzylthio)-5-trifluoromethylbenzoate (500 mg, 1.40 mmol) in N,N-dimethylformamide (10 ml). After stirring 30 minutes at 75° C., the mixture was poured into water (50 ml), the mixture brought to pH5 with 2N hydrochloric acid, the product extracted with diethyl ether, the combined extracts washed with water, dried (sodium sulfate), and evaporated. The residue was chromatographed on a column of silica gel (Merck 7734, packed as a slurry in 25:1 hexane-ether). Elution with 25:1 hexane-ether containing 1% acetic acid afforded the desired product as a white solid upon evaporation of the appropriate fractions; yield 385 mg (85%); m/z 324 (M+.).

EXAMPLE 16

3-Hydroxy-2-(m-methylphenyl)-5-trifluoromethylbenzo[b]thiophene

Step A: Preparation of 2-(m-methylbenzylthio)-5-trifluoromethylbenzoic acid

A mixture of m-methylbenzylmercaptan (3.36 g, 24.3 mmol), sodium methoxide (1.31 g, 24.3 mmol) and N,N-dimethylformamide (12.5 ml) was cooled to −15° C., and then added dropwise with stirring to a solution of 4-chloro-3-cyanobenzotrifluoride (5.0 g, 2.43 mmol), in N,N-dimethylformamide (7.5 ml). After stirring for 1 hour at room temperature under a nitrogen atmosphere, the mixture was added to cold water (175 ml) and extracted with chloroform. The organic extract was dried (sodium sulfate) and evaporated to give a pale yellow oil, which was taken up in ethanol (10 ml) and 20% aqueous sodium hydroxide (45 ml) and heated at reflux temperature for 24 hours. Concentration of the reaction mixture followed by diethyl ether extraction and evaporation gave an orange-red oil, that was suspended in water and acidified with 6N hydrochloric acid. The solid that separated out was filtered and dried by suction. The solid was recrystallized from diethyl ether; yield 5.95 g (75%). The 60 MHz NMR spectrum in chloroform-d was in accord with the desired structure.

Step B: Preparation of methyl 2-(m-methylbenzylthio)-5-trifluoromethylbenzoate

A mixture of 2-(m-methylbenzylthio)-5-trifluoromethylbenzoic acid (1.65 g, 5.06 mmol) and 1-aza-2-methoxy-1-cycloheptene (643 mg, 5.06 mmol) was heated at 80°–85° C. for 18 hours, cooled, diluted with diethyl ether, washed with 1N aqueous sodium hydroxide solution, water, dried (sodium sulfate), and evaporated. The product was crystallized from methanol; yield 885 mg (51%). The 60 MHz NMR spectrum in chloroform-d was in accord with the desired structure.

Step C: Preparation of 3-hydroxy-2-(m-methylphenyl)-5-trifluoromethylbenzo[b]thiophene To a slurry of sodium hydride (50% dispersion in mineral oil) (253 mg, 5.27 mmol) in N,N-dimethylformamide (3 ml) at 75° C. under a nitrogen atmosphere was added a solution of methyl 2-(m-methylbenzylthio)-5-trifluoromethylbenzoate (885 mg, 2.60 mmol) in N,N-dimethylformamide (12 ml). Gas evolution was observed during the 20 minute addition period. After stirring an additional 45 minutes at 75° C., water (70 ml) was added, and the aqueous mixture was brought to pH5–6 at room temperature with 2N hydrochloric acid. Extraction of the mixture with diethyl ether followed by washing the combined extracts with water and evaporation gave a residue that was chromatographed on a column of silica gel (Merck 7734, packed as a slurry in 15:1 hexane-ether). Elution with 15:1 hexane-ether containing 1% acetic acid and evaporation of the appropriate fractions afforded the product as a white crystalline solid; yield 450 mg (56%); m/z 308 (M+.); m.p. 124°–126°.

EXAMPLE 17

3-Acetoxy-5-chloro-2-phenylbenzo[b]thiophene

Employing the procedure described in Example 1, but substituting for the 2-bromohexanoic acid used in Step A thereof, an equivalent amount of α-bromophenylacetic acid, there were prepared in sequence:
Step A: 2-(2'-Carboxy-4'-chlorophenylthio)-phenylacetic acid
Step B: 3Acetoxy-5-chloro-2-phenylbenzo[b]thiophene; m.p. 111°–116° C.

EXAMPLE 18

5-Chloro-3-hydroxy-2-phenylbenzo[b]thiophene

A mixture of 3-acetoxy-5-chloro-2-phenylbenzo[b]thiophene (150 mg, 0.50 mmol) and 20% aqueous sodium hydroxide (5 ml) was stirred at reflux temperature for 1 hour. The cooled reaction mixture was acidified with concentrated hydrochloric acid, the solid that separated out filtered, washed with water, and dried in vacuo over phosphorous pentoxide. Recrystallization from cyclohexane afforded pure 5-chloro-3-hydroxy-2-phenylbenzo[b]thiophene; yield 35 mg (26%); m/z 275 (M+.).

EXAMPLE 19

Methyl 3-methoxybenzo[b]thiophene-2-acetate

Step A: Preparation of Methyl 3-methoxybenzo[b]thiophene-2-carboxylate

A stirred, ice-bath cooled mixture of methyl 3-hydroxybenzo[b]thiophene-2-carboxylate (*J. Org. Chem.* 32, 2678 (1967) (2.1 g, 0.01 m) and dry methylene chloride (25 ml) was treated with ethereal diazomethane in portions until the yellow color of the diazomethane persists, and nitrogen was no longer evolved. Concentration in vacuo yielded methyl 3-methoxybenzo[b]thiophene-2-carboxylate as a pale tan solid; m/z 324 (M+.). The material was used without further purification in the next step.

When the starting benzthiophene of the above example was replaced by methyl 3-hydroxy-5-(trifluoromethyl)benzo[b]thiophene-2-carboxylate, there was obtained methyl 3-methoxy-5-(trifluoromethyl)-benzo[b]thiophene-2-carboxylate as a pale yellow solid.

Step B: Preparation of 3-methoxybenzo[b]thiophene-2-carboxylic acid

A stirred suspension of methyl 3-methoxybenzo[b]thiophene-2-carboxylate (2.22 g, 0.01 m) in a mixture of methanol (35 ml) and water (5 ml) was treated over two minutes with 2.5N sodium hydroxide solution (8.0 ml, 0.02 m). The resulting suspension was covered with a nitrogen atmosphere and allowed to stir overnight at ambient temperatures. The filtered solution was then added in pipettesfull to a stirred excess dilute hydrochloric acid-ice mixture. The aged mixture was filtered and the cake washed well with water and dried to yield 2.0 g white solid with consistent NMR; m/z 208 (M+.).

When the starting benzothiophene of the above example was replaced by methyl 3-methoxy-5-(trifluoromethyl)benzo[b]thiophene-2-carboxylate, there was obtained 3-methoxy-5-(trifluoromethyl)-benzo[b]thiophene-2-carboxylic acid.

Step C: Preparation of methyl 3-methoxybenzo[b]thiophene-2-acetate (C-1) 3-Methoxybenzo[b]thiophene-2-carbonylchloride An ice-cooled suspension of 3-methoxybenzo[b]thiophene-2-carboxylic acid (0.62 g, 0.003 m) and dried methylene chloride (25 ml) was treated under nitrogen with thionyl chloride (2.0 ml) and dimethylformamide (1 drop). After stirring overnight two times at ambient temperatures, the volatiles were removed in vacuo, and the solid residue washed twice by addition and removal in vacuo of small portions of benzene. The resultant off-white solid was used without further purification in the next step.

(C2) Diazomethyl 3-methoxybenzo[b]thiophene-2-ylketone

The acid chloride from last step was taken up in a minimum of dried methylene chloride and added dropwise to ice-cold, stirred, excess diazomethane in ether. The resultant yellow mixture was allowed to stir cold for one hour, then at ambient temperatures overnight. Concentration in vacuo yielded the desired diazoketone as a yellow solid.

(C-3) Methyl 3-methoxybenzo[b]thiophen-2-acetate

To a stirred 100 ml portion of dried methanol was added ca. one quarter of a 0.4 g portion of Ag$_2$O. After 5 minutes, and additional ca 0.1 g of the silver oxide was added followed immediately by the diazoketone (1.2 g). The resultant vigorously stirred mixture was set in an oil-bath at 100° C. When refluxing commenced, the remaining silver oxide plus ca. 25 mg silver nitrate was added, and the mixture heated under reflux until no diazoketone remained (t.l.c. analysis). The cooled, filtered mixture was concentrated in vacuo, and the residue purified via column chromatography (silica gel, 50% methylene chloride-hexane as eluant) to yield methyl 3-methoxybenzo[b]thiophene-2-ylacetate as a pale yellow oil which crystallized on standing. The NMR was consistent with the structure. m/z 236 (M+.).

When 3-methoxy-5-(trifluoromethyl)benzo[b]thiophene-2-carboxylic acid was used in place of the starting benzthiophene of Example C-1, and carried through the same sequence of reactions, methyl 3-methoxy-5-(trifluoromethyl)benzo[b]thiophene-2-acetate is obtained.

EXAMPLE 20

Methyl 3-(3-hydroxybenzo[b]thiophen-2-yl)acrylate

To an ice-cold, stirred solution of thiosalicyclic acid methyl ester (1.68 g, 0.01 ml) in anhydrous methanol (40 ml) was added in one portion sodium methoxide (1.62 g, 0.03 m). After ca three minutes, the reaction is removed from the bath and allowed to stir at ambient temperatures for 10 minutes. The mixture was cooled, and methyl 4-bromocrotonate (1.99 g, 0.011 m) added dropwise over one minute. It was stirred cold ca. one hour, and then at ambient temperatures overnight. The resulting mixture was added in portions to a stirred ice-dilute hydrochloric acid-ether mixture and allowed to stir at room temperature. The ether layer was washed well with water, dried over sodium sulfate, filtered and concentrated to a pale tan crust. Trituration with methylene chloride yielded 1.7 g. methyl 3-(3-hydroxybenzothiophen-2-yl)-acrylate as a pale beige solid. m/z 234 (M+.); NMR (90 MHZ, CDCl$_3$+DMSO); δ3.70 s (CO$_2$CH$_3$); 5.90 d (=CH); 8.20 d (=CH).

When the starting thiosalicylate of the above example was replaced by 5-(trifluoromethyl)thiosalicyclic acid methyl ester, methyl 3-(3-hydroxy-5-(trifluoromethyl)-benzo[b]thiophene-2-yl)acrylate, an off-white solid m/z 302 (M+.) was obtained.

EXAMPLE 21

Methyl 3(3-acetoxybenzo[b]thiophen-2-yl)acrylate

To a stirred, ice-cooled solution of methyl 3-(3-hydroxybenzo[b]thiophen-2-yl)acrylate (0.23 g, 0.001 m) in dried pyridine (3.0 ml) was added acetic anhydride (0.2 ml) dropwise over ca. 0.5 minutes. After allowing to stir at ambient temperatures overnight, the mixture was added to a stirred mixture of ice-dilute hydrochloric acid-ether. The ether layer was washed well with water, dried over sodium sulfate, filtered and concentrated to a pale tan solid. m/z 276 (M+.); NMR (90 MHZ, CDCl$_3$): $\delta$2.38 s (OCOCH$_3$); 3.72 s (COOC$\underline{H}_3$).

When the corresponding 5-(trifluoromethyl)-3-hydroxybenzothiophene was used in the above reaction, methyl 3-(3-acetoxy-5-(trifluoromethyl)benzo[b]thiophene-2-yl)acrylate was obtained.

EXAMPLE 22

Methyl 3-(3-acetoxy-5-(trifluoromethyl)benzo[b]thiophen-3-yl)propionate

A stirred mixture of methyl 3-(3-acetoxy-5-(trifluoromethyl)benzo[b]thiophene-2-yl)acrylate (35 mg, 0.0001 m), ethyl acetate (10 ml), and 5% Pd/c (0.1 g) was set under a hydrogen atmosphere (1 atm.) until uptake was completed (ca. 8 minutes), filtered, and the filtrate concentrated in vacuo to yield methyl 3-(3-acetoxy-5-(trifluoromethyl)benzo[b]-thiophene-2-yl)propionate as a colorless oil. m/z 346 (M+.); NMR (90 MHZ, CDCl$_3$) $\delta$2.35 s (OCOCH$_3$); 2.60 t (—C$\underline{H}_2$); 3.08 t (—C$\underline{H}_2$); 3.65 s (CO$_2$CH$_3$).

When methyl 3-(3-acetoxybenzo[b]thiophene-2-yl)acrylate was reduced under the above conditions, methyl 3-(3-acetoxybenzo[b]thiophen-3yl)propionate was obtained as a colorless oil.

EXAMPLE 23

2-Methyl-3-Acetoxy-5-trifluoromethylbenzo[b]thiophene

Step A: Preparation of (2'-carboxy-4-trifluoromethylphenylthio)-propanoic acid

A solution of 8.19 g (34.7 mmol) of methyl 2-mercapto-5-trifluoromethylbenzoate and 6.38 g (41.7 mmol) of 2-bromopropanoic acid in 45 ml of 2.5M NaOH was heated at 80° for 2 hours. The solution was cooled, acidified to pH, with 2M H$_2$SO$_4$ and filtered to afford 9.68 g (95%) of white crystals, m.p. 185°–186° C.

The following compounds were prepared by the same procedure as described above:
2-(2'-carboxyphenylthio)propanoic acid, m.p. 192°–194° C., (97% yield).
2-(2'-carboxyphenyl-5-trifluoromethylphenylthio)-propanoic acid, m.p. 191°–193° C., (93% yield).
2-(2'-carboxy-4-trifluoromethylphenylthio)-3-methylbutanoic acid, m.p. 190°–191° C., (91% yield).

Step B: Preparation of 2-methyl-3-acetoxy-5-trifluoromethylbenzo[b]thiophene

A mixture of 9.00 g (30.6 mmol) of 2-(2'-carboxyphenylthio)propanoic acid and 9.00 g (110 mmol) of sodium acetate in 30 ml acetic anhydride was heated under reflux for 2 hours. The solution was concentrated and the residue was partitioned between ether and water. The ether layer was washed with NaHCO$_3$ and water, dried over Na$_2$SO$_4$, and evaporated to afford 7.72 g, (92%) of a white solid, m.p. 59°–60° C.

The following products were prepared by the same procedure as described above:
2-methyl-3-acetoxy-benzo[b]thiophene. NMR (CDCl$_3$, 90 MHz) $\delta$2.35 (s, 3H), 2.39 (s, 3H), 7.2–7.8 (m, 4H).
2-methyl-3-acetoxy-6-trifluoromethylbenzo[b]thiophene, m.p. 75°–77° C.
2-(1-methyl)ethyl-3-acetoxy-5-trifluoromethylbenzo[b]thiophene. NMR (CDCl$_3$, 200 mHz), $\delta$1.35 (d, 6H, J=7 Hz), 2.48 (s, 3H), 3.50 (m, 1H, J=7 Hz), 7.56 (d of d, 1H, J=1 Hz, J=9 Hz), 7.70 (s, 1H), 7.88 (d, 1H, J=9 Hz).

EXAMPLE 24

2-bromomethyl-3-acetoxybenzo[b]thiophene

A suspension of 1.00 g (4.85 mmol) of 2-methyl-3-acetoxybenzo[b]thiophene, 1.21 g (6.78 mmol) of N-bromosuccinimide, and 10 mg benzoylperoxide was heated under reflux for 3 hours. The mixture was filtered and the filtrate was concentrated to afford 1.42 g ,(100%) of a pale yellow oil. NMR (CDCl$_3$, 90 MHz) $\delta$2.35 (s, 3H, OAc), 4.48 (s, 2H, —C$\underline{H}_2$—Br), 7.2–7.8 (m, 4H).

The following compound was also prepared by the abovedescribed method:
2-bromomethyl-3-acetoxy-5-trifluoromethylbenzo[b]thiophene, m.p. 47°–49° C.

EXAMPLE 25

2-(3-acetoxybenzo[b]thien-2-ylmethyl)thio-4,5-diphenylimidazole

Potassium 4,5-diphenylimidazole-2-mercaptide was prepared by stirring a solution of 1.26 (5.00 mmol) of the thiol and 0.28 g (5.00 mmol) KOH in ethanol for 10 minutes and evaporating to dryness to afford 1.44 g (5 mmole) solid. This was mixed with 1.43 g (4.86 mmol) of 2-bromomethyl-3-acetoxybenzo[b]thiophene in 20 ml of ethyl acetate and stirred at 0° for 45 minutes. The solution was washed with water, dried over Na$_2$SO$_4$ and concentrated to an oil that was crystallized from ethyl acetate-hexane to afford 1.26 g (55%) of white needles, m.p. 144°–145° C.

Similarly, the following compounds were prepared:
2-(3-acetoxybenzo[b]thien-2-ylmethyl)thio-1,4-dimethyl imidazole, NMR (CDCl$_3$, 90 MHz) $\delta$2.17 (s, 3H), 2.30 (s, 3H, OAc), 3.34 (s, 3H, N—CH$_3$), 4.20 (s, 2H, S—C$\underline{H}_2$—), 6.53 (s, 1H), 7.1–7.7 (m, 4H).
2-(3-acetoxybenzo[b]thien-2-ylmethyl)thio-4-(2,2-dimethylethyl)-1-methylimidazole, NMR (CDCl$_3$, 90 MHz) 1.28 (s, 9H, C(CH$_3$)$_3$), 2.29 (s, 3H, OAc), 3.30 (s, 3H), 4.2 (s, 2H, —CH$_{12}$—S—), 6.50 (s, 1H), 7.1–7.8 (m, 4H).
2-(3-acetoxy-5-trifluoromethylbenzo[b]thien-2-ylmethyl)-thio-4,5-diphenylimidazole, m.p. 150°–152° C.
2-(3-acetoxy-5-trifluoromethylbenzo[b]thien-2-ylmethyl)thio-1,4-dimethylimidazole, NMR (CDCl$_3$, 90 MHz), $\delta$2.19 (s, 3H), 2.32 (s, 3H, OAc) 3.32 (s, 3H, N—CH$_3$), 4.25 (s, 2H, —C$\underline{H}_2$—S—), 6.55 (s, 1H), 7.3–7.9 (m, 3H).
2-(3-acetoxy-5-trifluoromethylbenzo[b]thien-2-ylmethyl)thio-4-(2,2-dimethylethyl)-1-methylimidazole, NMR (CDCl$_3$, 90 MHz) $\delta$1.30 (s, 9H, C(CH$_3$)$_3$), 2.35 (s, 3H, OAc), 4.25 (s, 2H, —C$\underline{H}_2$S), 6.50 (s, 1H), 7.3–7.9 (m, 3H).

EXAMPLE 26

2-(2,2-diphenylethenyl)-3-hydroxy-5-trifluoromethyl-benzo[b]thiophene

Step A: Preparation of Methyl 2-(3,3-diphenylprop-2-enylthio)-5-trifluoromethylbenzoate A solution of 2.19 g (9.86 mmol) of methyl 2-mercapto-5-trifluoromethylbenzoate, 2.29 g (10.0 mmol) of 1,1-diphenyl-3-chloro-1-propene, and 1.67 g (11.0 mmol) of diazabicycloundecene (DBU) in 10 ml tetrahydrofuran was stirred for 60 minutes at room temperature. The solution was partitioned between ether and water and the ether layer was washed with water, dried over $MgSO_4$ and evaporated. The residue was chromatographed (20% $CH_2Cl_2$-hexane) on silica to afford 3.6 g (85%) of a clear oil. NMR ($CDCl_3$, 90 MHz) 3.67 (d, 2H, J=8, $CH_2$), 3.92 (s, 3H, —$OCH_3$), 6.05 (t, 1H, J=8), 6.9–7.6 (m, 12H), 8.13 (s, 1H).

Step B: Preparation of 2-(2,2-diphenylethenyl)-3-hydroxy-5-trifluoromethyl-benzo[b]thiophene A solution of 1.64 ml (10.6 mmol) of N,N-diisopropylamine in 10 ml tetrahydrofuran was cooled to −20° C. under argon and 6.64 ml of 1.6M butyllithium in hexane was added. The solution was stirred at −22° C. for 15 minutes and then was warmed to 0°. A solution of 2.00 g (4.67 mmol) of methyl 2-(3,3-diphenylprop-2-enylthio)-5-trifluoro methylbenzoate was added and the mixture was stirred at room temperature for 2 hours.

The solution was poured onto 100 ml of 0.08M HCl and extracted into ether. The ether layer was washed with water, dried over $MgSO_4$ and evaporated to an oil that crystallized from methylene chloridehexane to afford 1.32 g (70%) of air-sensitive white crystals, m.p. 142° (decomp.)

EXAMPLE 27

2-(2,2-diphenylethenyl)-3-acetoxy-5-trifluoromethyl benzo[b]thiophene

A solution of 1.11 g (2.80 mmol) of 2-(2,2-diphenylethenyl)-3-hydroxy-5-trifluoromethylbenzo[b]thiophene, 0.5 ml acetic anhydride, and 0.2 ml pyridine in 5 ml methylene chloride was stirred under argon for 30 minutes. The solution was extracted into ether and the ether layer was washed with dilute $H_2SO_4$, $K_2CO_3$ and water, then dried over $MgSO_4$ and evaporated. The residue was crystallized from hexane to afford 0.525 g (43%) of tan needles, m.p. 159°–160° C.

C. Utility of the Compounds Within the Scope of the Invention

This invention also relates to a method of treatment for patients (or mammalian animals raised in the dairy, meat, or fur industries or as pets) suffering from disorders or diseases mediated by the inhibition of the oxidation of arachiodonic acid and/or leukotrienes, and gastric irritation or lesion. More specifically, this invention is directed to a method of treatment involving the administration of one or more of the enzyme inhibitors of formula (I) as the active constituent.

Accordingly, a compound of Formula (I) can be used among other things to reduce pain and inflammatory conditions, including rheumatoid arthritis, osteoarthritis, gout, psoriasis, inflammatory bowel disease and inflammation in the eye that may be caused by ocular hypertension and may eventually lead to glaucoma. It can also be used to correct respiratory, cardiovascular, and intravascular alterations or disorders, and to regulate immediate hypersensitivity reactions that cause human asthma and allergic conditions.

For the treatment of inflammation, arthritis conditions, cardiovascular disorder, allergy, psoriasis, asthma, or other diseases mediated by prostaglandins and/or leukotrienes, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or more perservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are coca butter and polyethylene glycols.

For topical use, creams, ointments, jellies, solutions or suspensions, etc., containing the anti-inflammatory agents are employed.

Dosage levels of the order from about 1 mg to about 100 mg per kilogram of body weight per day are useful in the treatment of the above-indicated conditions (from about 50 mg to about 5 gms. per patient per day). For example, inflammation is effectively treated and antipyretic and analgesic activity manifested by the administration from about 2.5 to about 75 mg of the compound per kilogram of body weight per day (about 75 mg to about 3.75 gms per patient per day).

D. Biological Data Supporting the Utility of the Compound Within the Scope of the Invention The following is a summary of biological data from standard bioassays. These data serve to illustrate that the compound of formula (I), for example, 3-acetoxy-2-butyl-5-chlorobenzo[b]thiophene, are useful in the treatment of leukotriene mediated diseases.

TABLE I

| Inhibition of RBL Cell 5-Lipoxygenase | |
|---|---|
| Compound | Percent Inhibition (conc.) |
| Example 1 | >95 (15 μM) |
| Example 2 | >95 (15 μM) |
| Example 4 | >95 (5 μM) |
| Example 5 | >95 (15 μM) |
| Example 6 | >95 (15 μM) |
| Example 7 | >95 (1 μM) |
| Example 8 | >95 (15 μM) |
| Example 11 | >95 (15 μM) |
| Example 12 | >95 (15 μM) |
| Example 15 | >95 (15 μM) |
| Example 16 | >95 (1 μM) |
| Example 18 | >95 (15 μM) |
| Example 20 | 100 (3.6 μM) |
| Example 21 | 71 (0.036 μM) |
| Example 22 | >95 (0.06 μM) |
| Example 23 | 100 (0.4 μM) |
| Example 25 | 52 (22 μM) |
| Example 27 | 95 (22 μM) |

Protocol published in R. W. Egan et al., "Advances in Prostaglandin, Thromboxane, and Leukotriene Research," Vol. 11 (edited by B. Samuelson et al., Raren Press, N.Y., 1983), p. 151.

What is claimed is:

1. A compound of formula:

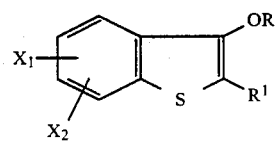

or a pharmaceutically acceptable salt thereof wherein $X_1$ and $X_2$ independent are;

(a) H;
(b) C$_{1-6}$alkyl;
(c) halo;
(d) haloC$_{1-6}$alkyl;
(e) OH;
(f) —OCOCH$_3$;
(g) —OC$_{1-6}$alkyl; or
(h) —OC$_{1-6}$alkylphenyl;

R$^1$ is
(a) C$_{1-6}$alkyl;
(b) phenyl of formula

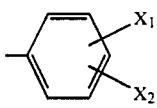

wherein X$_1$ and X$_2$ independent are halo, —CF$_3$, CH$_3$O—, CH$_3$—, CH$_3$S—, CH$_3$CO or CH$_3$COO—;

(c) benzyl of formula

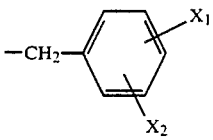

(d)

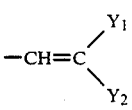

wherein Y$_1$ and Y$_2$ independently are phenyl as previously defined,
(e) C$_{1-6}$alkenyl;

R is
(a) H;
(b) —COCH$_3$;
(c) C$_{1-6}$alkyl; or
(d) benzyl.

2. The compound of claim 1 which is of formula:

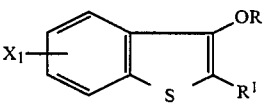

wherein X$_1$, R and R$^1$ are as previously defined.

3. The compound of claim 1 which is
3-Acetoxy-2-Butyl-5-Chlorobenzo[b]thiophene;
3-Acetoxy-2-Benzyl-5-Chlorobenzo[b]thiophene;
2-Benzyl-5-Chloro-3-Hydroxybenzo[b]thiophene;
3-Hydroxy-2-Phenyl-5-Trifluoromethylbenzo[b]thiophene;
3-Acetoxy-2-Phenyl-5-Trifluoromethylbenzo[b]thiophene;
3-Hydroxy-4-Methoxy-2-Phenylbenzo[b]thiophene;
3,4-Diacetoxy-2-Phenylbenzo[b]thiophene;
3,4-Dihydroxy-2-Phenylbenzo[b]thiophene;
3-Hydroxy-4-Isopropoxy-2-Phenylbenzo[b]thiophene;
4-Benzyloxy-3-Hydroxy-2-Phenylbenzo[b]thiophene;
3-Hydroxy-5-Trifluoromethyl-2-(m-trifluoromethylphenyl)-Benzo[b]thiophene;
3-Hydroxy-2-(m-chlorophenyl)-5-trifluoromethylbenzo[b]thiophene;
3-Hydroxy-2-(2,6-dimethylphenyl)-5-trifluoromethylbenzo[b]thiophene;
3-Hydroxy-2-(p-methylphenyl)-5-trifluoromethylbenzo[b]thiophene;
3-Hydroxy-2-(p-methoxyphenyl)-5-trifluoromethylbenzo[b]thiophene;
3-Hydroxy-2-(m-methylphenyl)-5-trifluoromethylbenzo[b]thiophene;
3-Acetoxy-5-chloro-2-phenylbenzo[b]thiophene;
5-Chloro-3-hydroxy-2-phenylbenzo[b]thiophene;
Methyl 3-methoxybenzo[b]thiophene-2-acetate;
Methyl 3-(3-hydroxybenzo[b]thiophen-2-yl)acrylate;
Methyl 3(3-acetoxybenzo[b]thiophen-2-yl)acrylate;
Methyl 3-(3-acetoxy-5-(trifluoromethyl)benzo[b]thiophen-3-yl)propionate;
2-Methyl-3-Acetoxy-5-trifluoromethylenzo[b]thiophene;
2-Bromomethyl-3-acetoxybenzo[b]thiophene;
2-(2,2-diphenylethenyl)-3-hydroxy-5-trifluoromethylbenzo[b]thiophene;
2-(2,2-diphenylethenyl)-3-acetoxy-5-trifluoromethylbenzo[b]thiophene.

4. The compound of claim 1 which is Methyl 3-(3-acetoxybenzo[b]thiophen-2-yl)acrylate.

5. The compound of claim 1 which is Methyl 3-(3-acetoxy-5-(trifluoromethyl)benzo[b]thiophen-3-yl)propionate.

6. The compound of claim 1 which is 2-Methyl-3-Acetoxy-5-trifluoromethylbenzo[b]thiophene.

7. The compound of claim 1 which is Methyl 3-(3-hydroxybenzo[b]thiophen-2-yl)acrylate.

8. A pharmaceutical composition for treating inflammation, fever and pain in mammalian species comprising a pharmaceutically acceptable carrier and an effective amount of a compound of formula:

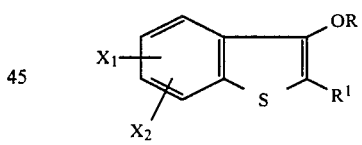

or a pharmaceutically acceptable salt thereof wherein X$_1$ and X$_2$ independently are;
(a) H;
(b) C$_{1-6}$alkyl;
(c) halo;
(d) haloC$_{1-6}$alkyl;
(e) OH;
(f) —OCOCH$_3$;
(g) —OC$_{1-6}$alkyl; or
(h) —OC$_{1-6}$alkylphenyl;

R$^1$ is
(a) C$_{1-6}$alkyl;
(b) phenyl of formula

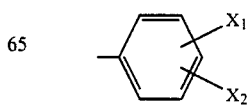

wherein $X_1$ and $X_2$ independently are halo, —$CF_3$, $CH_3O$—, $CH_3$—, $CH_2S$—, $CH_3CO$ or $CH_3COO$—;

(c) benzyl of formula

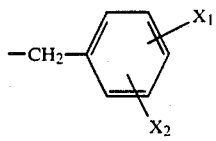

(d)

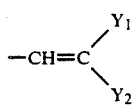

wherein $Y_1$ and $Y_2$ independent are phenyl as previously defined;

(e) $C_{1-6}$alkenyl;

R is (a) H;
(b) —$COCH_3$;
(c) $C_{1-6}$alkyl; or
(d) benzyl.

9. The pharmaceutical composition of claim 8 wherein the compound is of formula:

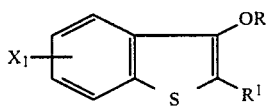

wherein $X_1$, $X_2$ R and $R^1$ are as previously defined.

10. The composition of claim 9 wherein the active compound is
3-Acetoxy-2-Butyl-5-Chlorobenzo[b]thiophene;
3-Acetoxy-2-Benzyl-5-Chlorobenzo[b]thiophene;
2-Benzyl-5-Chloro-3-Hydroxybenzo[b]thiophene;
3-Hydroxy-2-Phenyl-5-Trifluoromethylbenzo[b]thiophene;
3-Acetoxy-2-Phenyl-5-Trifluoromethylbenzo[b]thiophene;
3-Hydroxy-4-Methoxy-2-Phenylbenzo[b]thiophene;
3,4-Diacetoxy-2-Phenylbenzo[b]thiophene;
3,4-Dihydroxy-2-Phenylbenzo[b]thiophene;
3-Hydroxy-4-Isopropoxy-2-Phenylbenzo[b]thiophene;
4-Benzyloxy-3-Hydroxy-2-Phenylbenzo[b]thiophene;
3-Hydroxy-5-Trifluoromethyl-2-(m-trifluoromethylphenyl)-Benzo[b]thiophene;
3-Hydroxy-2-(m-chlorophenyl)-5-trifluoromethylbenzo[b]thiophene;
3-Hydroxy-2-(2,6-dimethylphenyl)-5-trifluoromethylbenzo[b]thiophene;
3-Hydroxy-2-(p-methylphenyl)-5-trifluoromethylbenzo[b]thiophene;
3-Hydroxy-2-(p-methoxyphenyl)-5-trifluoromethylbenzo[b]thiophene;
3-Hydroxy-2-(m-methylphenyl)-5-trifluoromethylbenzo[b]thiophene;
3-Acetoxy-5-chloro-2-phenylbenzo[b]thiophene;
5-Chloro-3-hydroxy-2-phenylbenzo[b]thiophene;
Methyl 3-methoxybenzo[b]thiophene-2-acetate;
Methyl 3-(3-hydroxybenzo[b]thiophen-2-yl)acrylate;
Methyl 3-(3-acetoxybenzo[b]thiophen-2-yl)acrylate;
Methyl 3-(3-acetoxy-5-(trifluoromethyl)benzo[b]thiophen-3-yl)propionate;
2-Methyl-3-Acetoxy-5-trifluoromethylenzo[b]thiophene;
2-Bromomethyl-3-acetoxybenzo[b]thiophene;
2-(2,2-diphenylethenyl)-3-hydroxy-5-trifluoromethylbenzo[b]thiophene;
2-(2,2-diphenylethenyl)-3-acetoxy-5-trifluoromethylbenzo[b]thiophene.

11. The composition of claim 9 wherein the active compound is Methyl 3-(3-acetoxybenzo[b]thiophen-2-yl)acrylate.

12. The composition of claim 9 wherein the active compound is Methyl 3-(3-acetoxy-5-(trifluoromethyl)-benzo[b]thiophen-3-yl)-propionate.

13. The composition of claim 9 wherein the active compound is 2-Methyl-3-Acetoxy-5-trifluoromethylbenzo[b]thiophene.

14. The composition of claim 9 wherein the active compound is Methyl 3-(3-hydroxybenzo[b]thiophen-2-yl)acrylate.

15. A method for the treatment of inflammation, fever and pain commprising the administration to a mammalian species in need of such treatment an effective amount of a compound of formula (I):

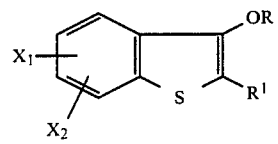

or a pharmaceutically acceptable salt thereof wherein $X_1$ and $X_2$ independently are:

(a) H;
(b) $C_{1-6}$alkyl;
(c) halo;
halo$C_{1-6}$alkyl;
(e) OH;
(f) —$OCOCH_3$;
(g) —$OC_{1-6}$alkyl; or
(h) —$OC_{1-6}$alkylphenyl;

$R^1$ is (a) $C_{1-6}$alkyl;
(b) phenyl of formula

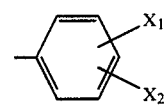

wherein $X_1$ and $X_2$ independent are halo, —$CF_3$, $CH_3O$—, $CH_3$—, $CH_3S$—, $CH_3CO$ or $CH_3COO$—;

(c) benzyl of formula

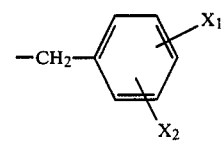

(d)

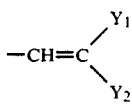

wherein $Y_1$ and $Y_2$ independently are phenyl as previously defined,
(e) $C_{1-6}$alkenyl;

R is
(a) H;
(b) —COCH$_3$;
(c) $C_{1-6}$alkyl; or
(d) benzyl.

16. The method of claim 15 wherein the compound is of formula:

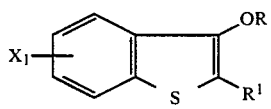

wherein $X_1$, R and $R^1$ are as previously defined.

17. The method of claim 7 wherein the active compound is
3-Acetoxy-2-Butyl-5-Chlorobenzo[b]thiophene;
3-Acetoxy-2-Benzyl-5-Chlorobenzo[b]thiophene;
2-Benzyl-5-Chloro-3-Hydroxybenzo[b]thiophene;
3-Hydroxy-2-Phenyl-5-Trifluoromethylbenzo[b]thiophene;
3-Acetoxy-2-Phenyl-5-Trifluoromethylbenzo[b]thiophene;
3-Hydroxy-4-Methoxy-2-Phenylbenzo[b]thiophene;
3,4-Diacetoxy-2-Phenylbenzo[b]thiophene;
3,4-Dihydroxy-2-Phenylbenzo[b]thiophene;
3-Hydroxy-4-Isopropoxy-2-Phenylbenzo[b]thiophene;
4-Benzyl-3-Hydroxy-2-Phenylbenzo[b]thiophene;
3-Hydroxy-5-Trifluoromethyl-2-(m-trifluoromethylphenyl)-Benzo[b]thiophene;
3-Hydroxy-2-(m-chlorophenyl)-5-trifluoromethylbenzo[b]thiophene;
3-Hydroxy-2-(2,6-dimethylphenyl)-5-trifluoromethylbenzo[b]thiophene;
3-Hydroxy-2-(p-methylphenyl)-5-trifluoromethylbenzo[b]thiophene;
3-Hydroxy-2-(p-methoxyphenyl)-5-trifluoromethylbenzo[b]thiophene;
3-Hydroxy-2-(m-methylphenyl)-5-trifluoromethylbenzo[b]thiophene;
3-Acetoxy-5-chloro-2-phenylbenzo[b]thiophene;
5-Chloro-3-hydroxy-2-phenylbenzo[b]thiophene;
Methyl 3-methoxybenzo[b]thiophene-2-acetate;
Methyl 3-(3-hydroxybenzo[b]thiophen-2-yl)acrylate;
Methyl 3-(3-acetoxybenzo[b]thiophen-2-yl)acrylate;
Methyl 3-(3-acetoxy-5-(trifluoromethyl)benzo[b]thiophen-3-yl)-propionate;
2-Methyl-3-Acetoxy-5-trifluoromethylenzo[b]thiophene;
2-Bromomethyl-3-acetoxybenzo[b]thiophene;
2-(2,2-diphenylethenyl)-3-hydroxy-5-trifluoromethylbenzo[b]thiophene;
2-(2,2-diphenylethenyl)-3-acetoxy-5-trifluoromethylbenzo[b]thiophene.

18. The method of claim 7 wherein the active compound is Methyl 3-(3-acetoxybenzo[b]thiophen-2-yl)acrylate.

19. The method of claim 7 wherein the active compound is Methyl 3-(3-acetoxy-5-(trifluoromethyl)benzo[b]thiophen-3-yl)-propionate.

20. The method of claim 7 wherein the active compound is 2-Methyl-3-Acetoxy-5-trifluoromethylbenzo[b]thiophene.

21. The method of claim 7 wherein the active compound is Methyl 3-(3-hydroxybenzo[b]thiophen-2-yl)acrylate.

* * * * *